(12) United States Patent
Stefan et al.

(10) Patent No.: US 12,290,941 B2
(45) Date of Patent: May 6, 2025

(54) END EFFECTOR, DEVICE FOR CONTROLLING A ROBOT END EFFECTOR AND MEDICAL TELEMANIPULATION SYSTEM

(71) Applicant: KARL STORZ SE & Co. KG, Tuttlingen (DE)

(72) Inventors: Jochen Stefan, Tuttlingen (DE); Sven Axel Grüner, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 440 days.

(21) Appl. No.: 17/869,849

(22) Filed: Jul. 21, 2022

(65) Prior Publication Data

US 2023/0034550 A1 Feb. 2, 2023

(30) Foreign Application Priority Data

Jul. 28, 2021 (DE) .................... 10 2021 119 559.4

(51) Int. Cl.
*B25J 9/16* (2006.01)

(52) U.S. Cl.
CPC .................................. *B25J 9/1689* (2013.01)

(58) Field of Classification Search
CPC .............. A61B 17/295; A61B 17/3201; A61B 2017/00353; A61B 2017/2929; A61B 2017/2938; A61B 2034/302; A61B 2034/305; A61B 34/30
See application file for complete search history.

(56) References Cited

U.S. PATENT DOCUMENTS

2015/0313676 A1* 11/2015 Deodhar ................ A61B 34/30
606/130

FOREIGN PATENT DOCUMENTS

| WO | WO 2014/030110 A1 | 2/2014 |
| WO | WO 2019/099584 A | 5/2019 |

OTHER PUBLICATIONS

Office Action for corresponding German Patent Application No. 10 2021 119 559.4, mailed Mar. 7, 2022.

* cited by examiner

*Primary Examiner* — Mark D Remaly
(74) *Attorney, Agent, or Firm* — Jason H. Vick; Amped IP LLC

(57) ABSTRACT

An exemplary embodiment relates to an end effector (1), in particular a robot end effector, a device (20) with an operating element (25) for controlling an end effector (1), a robot with at least one end effector (1) and a medical telemanipulation system.

19 Claims, 7 Drawing Sheets

END EFFECTOR, DEVICE FOR CONTROLLING A ROBOT END EFFECTOR AND MEDICAL TELEMANIPULATION SYSTEM

CROSS-REFERENCE TO RELATED APPLICATIONS

This application claims the benefit under 35 U.S.C. 119(a) to German Patent Application No. 10 2021 119 559.4, filed 28 Jul. 2021, the disclosure of which is incorporated herein by reference in its entirety.

BACKGROUND

An exemplary aspect relates to an end effector, in particular a robot end effector, having a first branch and a second branch and a component at least partially accommodating the two branches. Furthermore, an exemplary aspect relates to a device with an operating element for controlling an end effector. Furthermore, an exemplary aspect relates to a robot with at least one end effector. Furthermore, an exemplary aspect relates to a medical telemanipulation system with an end effector and/or a device.

End effectors, in particular robot end effectors, are known from the state of the art. In robotics, the last element of a kinematic chain is called the end effector. A surgical robot is usually located at an operating table and has a number of arms to which a 3D endoscope and instruments (referred to below as end effectors) are attached. These end effectors can be inserted into a patient's body via trocars. They are used there to perform an endoscopic operation. At their distal end, the end effectors have two tools that are designed like grippers and can be moved towards one another, which are known as branches, jaw parts or gripper jaw parts. Furthermore, the end effectors have mechanical devices for controlling the tip orientation and rotational orientation in space immediately behind the distal tool tip, which can be controlled and operated by a motor of a robot.

Medical telemanipulation systems are mainly used to perform difficult operations and, above all, sewing work in places inside the human body that are difficult to access. Such medical telemanipulation systems have, among other things, an input unit that the operator can operate. The input unit comprises two input apparatuses, which the surgeon respectively reaches into with the thumb and another finger. The input apparatus detects the movement of the hands and transmits their position and orientation in space as well as the opening status of the input unit to a controlling software.

The telemanipulation system now converts the detected hand position into a movement of a robot as well as the tip and tool position of the end effector in "real time", as described above. The telemanipulation system then controls the robot and the end effectors via servomotors in such a way that the movement and position of the branches/jaw parts or their gripper surfaces (e.g., in a patient's body) always correspond to those of the input unit.

In the case of the known end effectors, the jaw parts can only be opened and closed in the manner of forceps. As a result, the position of an object, such as a needle, which is held between the jaw parts, can only be changed by the object being clamped by the second end effector and having to be gripped with forceps that are actually provided.

Given this background, one exemplary aspect is to develop a mechanism that makes it possible to change the orientation of an object, such as a needle, that is clamped by the branches or jaw parts, without releasing or gripping the branches or jaw parts to be grasped. In addition, an input option should be provided to control this mechanism.

This object is achieved with the features of independent claim 1 with regard to the end effector, with the features of claim 9 with regard to the device, with the features of claim 15 with regard to the robot and with the features of claim 16 with regard to the medical telemanipulation system.

To solve this object, an end effector is proposed, in particular a robot end effector, comprising a first branch and a second branch and a component at least partially accommodating the second branch, in particular an end effector or effector fork, the first branch along a direction of longitudinal extension of the component and/or the end effector is displaceable relative to the second branch, wherein the first branch is connected to a first displacement means for relative displacement and wherein the second branch is rotatably mounted on the component for clamping or for holding an object between the two branches, wherein the second branch is displaced or rotated, the second branch is rotatably connected to a displacement element, in particular by means of a joint, or the second branch, in particular pressure, force, or compressive force is applied rotatably to the displacement element.

By providing the end effector, it is possible to change the orientation of an object clamped by the branches or jaw parts, such as a needle, without releasing or gripping the clamping of the branches or jaw parts.

A direction of longitudinal extension of the component or of the end effector can be understood to mean a longitudinal direction, a longitudinal extension or an axial direction of the component or of the end effector. A relative displacement can be understood to mean a relative displacement or translatory displacement. "Being connected" can be understood to mean "being arranged".

The first displacement means is preferably designed as a pressure and tensile element or as a torque-transmitting element. The first displacement means is preferably a wire rope.

The displacement element is preferably arranged within the component. The displacement element can also be understood as an actuating element. More preferably, the displacement element has a stop. The stop is preferably arranged on the branch side. The first displacement means is preferably set up to be displaced. More preferably, the displacement element is set up to be displaced.

In a particularly preferred manner, the second branch can apply or strike pressure, force, or compressive force against the displacement element. For this purpose, the end effector can comprise a spring. The spring can be set up to hold the second branch in a zero position or closed position or to return it to this. For example, the spring can be arranged on a joint connecting the component and the second branch between the component and the second branch.

With a relative displacement of the first branch to the second branch, the first branch is arranged to be displaced from a first position to a second position. When the second branch is twisted, the second branch is set up to be twisted from a first position into a second position.

The displacement element can preferably be displaced in the direction of longitudinal extension of the component. More preferably, the displacement element is arranged to be displaceable within the component.

In one embodiment, in order to displace the first branch relative to the second branch, the first branch has a section which is designed as a counterpart to a section of the displacement element. This makes it possible to move the first branch relative to the second branch, for example along a surface.

The first displacement means is preferably connected to a first end of the first branch in a manner that is resistant to tension and pressure.

More preferably, the displacement element is connected to a second displacement means. This makes it possible to achieve a rotary movement of the second branch. In other words, the second branch can be rotated or twisted relative to the first branch. In still other words, the second branch can be rotated or twisted with respect to the first branch. The displacement element is preferably arranged between the second displacement means and the second branch.

More preferably, the second displacement means is a pressure and tensile element. The second displacement means is preferably a wire rope.

The end effector is particularly and preferably set up to displace the displacement element, in particular in the direction of longitudinal extension of the component, when the second displacement means is displaced. As described above, this results in a torsion or rotation of the second branch in the direction towards the first branch and/or in the direction away from the first branch. Preferably, the displacement element itself undergoes an axial displacement.

In a particularly advantageous embodiment, the first displacement means is rotatably connected to a first end of the first branch, wherein the first displacement means is arranged in a rotationally fixed manner in a screw sleeve, wherein the screw sleeve is arranged rotatably in the displacement element, and wherein the displacement element is used to move the displacement element in a thread of the screw sleeve with a complementary counter-thread. This makes it possible, as a result of a rotary movement of the first displacement means, to displace the displacement element, which is connected to the second branch, preferably within the component, without changing a position of the first branch.

The first displacement means is preferably a pressure and tensile element and a torque-transmitting element. The first displacement means is preferably a wire rope.

The first displacement means is preferably arranged in a displacement means sleeve having a collar, wherein the first displacement means is connected to the displacement means sleeve in a rotationally fixed manner. This makes it possible to rotatably connect the first displacement means to the first branch and to exert a tension and/or pressure force on the first branch.

A collar of the displacement means sleeve can be understood to mean a projecting section.

The screw sleeve particularly and preferably has a collar, wherein the screw sleeve is arranged in the component such that it can rotate. This makes it possible to clamp the screw sleeve axially and firmly in the component without preventing turning or rotation of the first displacement means.

A collar of the screw sleeve can be understood to mean a projecting section.

More particularly and preferably, the end effector is set up to displace the displacement element, in particular in the direction of longitudinal extension of the component, when the first displacement means rotates about a longitudinal axis of the first displacement means.

According to one embodiment, a device with an operating element for controlling an end effector is proposed, as described above. A device can be understood as an input unit. The operating element can be understood as an input apparatus.

The operating element preferably has a housing and two limbs arranged on the housing, with at least one of the limbs having an actuating means which is set up to displace the first branch relative to the second branch. This makes it possible to displace the first branch relative to the second branch as if a needle held by the branches were being twisted.

A component that is displaceably arranged within the housing and in particular that transmits force is preferably provided. The limbs on the housing are preferably designed to be rotatable, wherein the device has two lugs connecting the limbs to the component for actuating the component. As a result of the actuation of the component, the second branch can be twisted or rotated in the direction towards the first branch and/or in the direction away from the first branch.

A distal end of the component particularly and preferably protrudes from the housing.

In a preferred embodiment, the actuating means is a slider, wherein the slider is displaceable along the longitudinal extension of the limb. The direction of longitudinal extension can be understood as meaning a direction of longitudinal extension, a longitudinal direction or an axial direction.

More preferably, the limb comprises a corrugation and/or at least one stop for limiting displacement of the slider and/or a spring for returning the slider into its initial position. Furthermore, a magnet can be integrated into the slider and a displacement sensor can be integrated into the limb.

A displacement of the slider can be limited by means of the stop. The slider can be returned into its initial position in a simple manner by means of the spring. A position of the slider can be detected by means of the magnet and the position sensor. Preferably a Hall sensor can be used, which is why a magnet is integrated into the slider.

In a further preferred embodiment, the actuating means is a friction wheel, wherein the friction wheel is arranged in or on the limb. This allows the actuating means to be displaced in a simple manner.

The friction wheel is preferably arranged in a recess, in particular a trough, of the limb. Preferably, the limb or the friction wheel comprises at least one stop to limit torsion or rotation of the friction wheel and/or a spring to return the friction wheel to its initial position. Furthermore, an angle sensor can be integrated into the limb.

By providing the recess in the limb, the friction wheel can be operated in a simple manner. By providing the stop, torsion or rotation of the friction wheel can be limited in a simple manner. The provision of the spring allows the friction wheel to be returned to its initial position in a simple manner. By providing the angle sensor, a rotation angle can be detected, wherein the detected value is able to be used to control the first branch and thus for the relative displacement of the first branch.

Detected values, which have been detected by means of the displacement or angle sensor, can be transmitted from the device to a medical telemanipulation system via a connection, in particular a cable.

Preferably at least one of the limbs has a finger or thumb ring. By providing the finger or thumb ring, the device is easily operable.

Furthermore, according to one embodiment, a robot with at least one end effector is proposed, as described above, and/or at least one device, preferably two devices, as described above.

A medical telemanipulation system is also proposed according to this disclosure. The medical telemanipulation system comprises at least one device, preferably two devices, as described above, and/or a robot, as described above.

Furthermore, the medical telemanipulation system can comprise servomotors. The telemanipulation system is preferably set up to control the robot as well as the end effectors via the servomotors in such a way that the movement and position of the branches/jaw parts or their gripper surfaces, e.g., in a patient's body, always correspond to that of the input unit (device). A synchronous process can thus be carried out in a simple manner.

BRIEF DESCRIPTION OF THE DRAWINGS

Further advantages and details of the invention result from the following description of preferred embodiments of the invention and from the drawings.

They show.

DETAILED DESCRIPTION

Identical elements or elements with the same function are provided with the same reference symbols in the figures.

Figure 1:
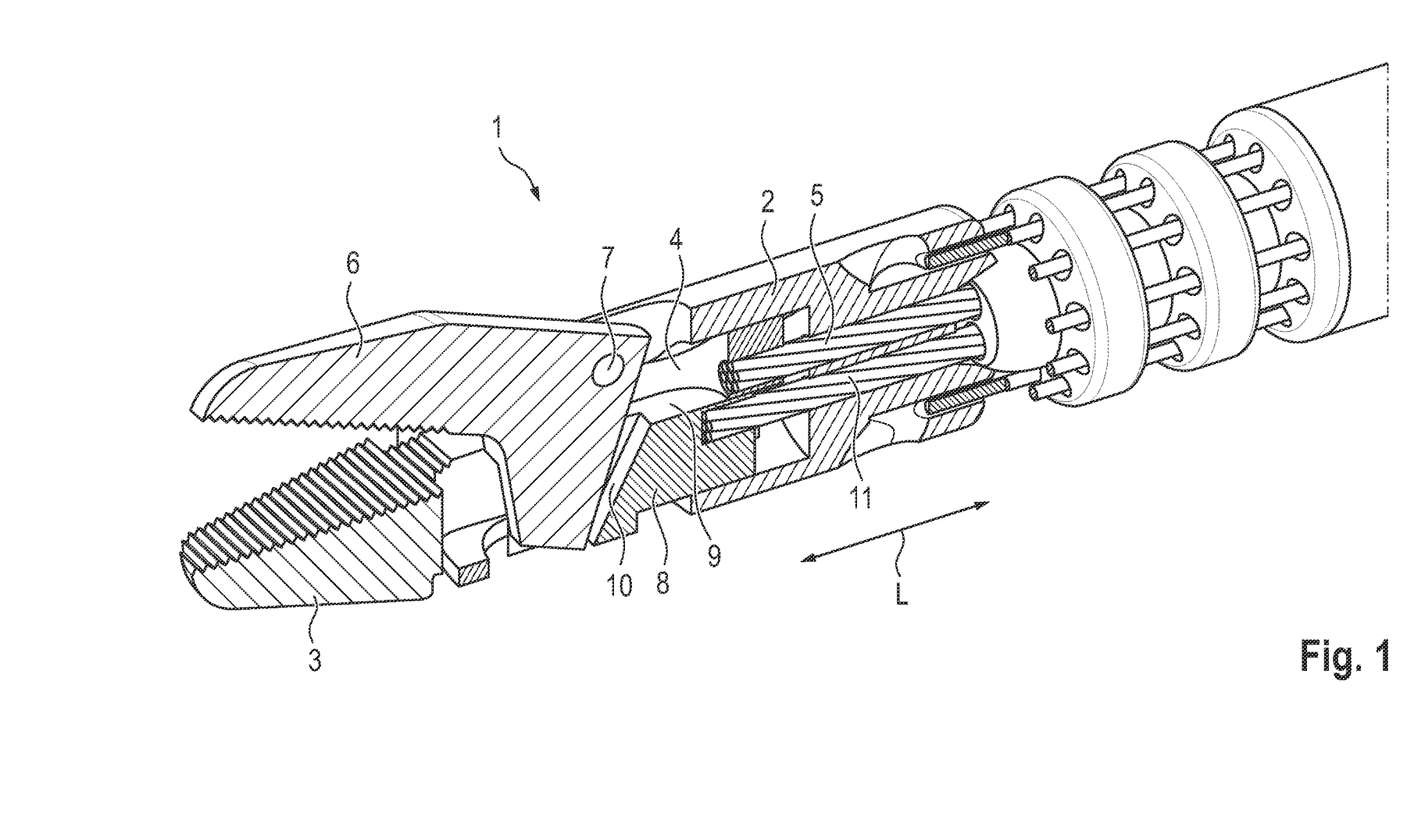
FIG. 1: a section through a first embodiment of an end effector.

The end effector 1 shown in FIG. 1, in particular a robot end effector, comprises a first branch 3 and a second branch 6 as well as a component 2 that at least partially accommodates the two branches 3 and 6. The component 2 can be understood as an end effector or effector fork. The component 2 is used to guide branches 3 and 6.

The first branch 3 is arranged to be displaceable relative to the second branch 6 along a direction of extension L of the component 2 or of the end effector 1. The first branch 3 is connected to a displacement means 5 for relative displacement. The displacement means 5 is designed as a rope, in particular as a wire rope.

The second branch 6 is rotatably mounted on the component 2 for clamping an object between the two branches 3, 6. The object is preferably clamped between the gripped grip areas of both branches 3, 6. The object can be a needle, for example. The second branch 6 is rotatably connected to a displacement element 8 for torsion or rotating the second branch 6. In order to enable torsion or rotation of the second branch 6, the second branch 6 is connected to the component 2 by means of a joint or pivot point 7.

In order to displace the first branch 3 relative to the second branch 6, the first branch 3 has a section 4 which is designed as a counterpart to a section 9 of the displacement element 8. The displacement element 8 has a stop 10. The stop 10 is set up to only allow a torsion or rotation of the second branch 6 up to a certain point. In other words, the stop 10 serves to limit an opening angle of the second branch 6.

The displacement element 8 is connected to a second displacement means 11. The second displacement means 11 is designed as a rope, in particular a wire rope. In addition to the distal end of the first displacement means 5 shown, the second distal end of the second displacement means 11 shown is also guided within the component 2. Both displacement means 5 and 11 are oriented in accordance with the direction of longitudinal extension of the component 2 or of the end effector 1.

According to the first embodiment, a second displacement means 11 is used in addition to a first displacement means 5, both displacement means 5 and 11 running parallel to one another. An axial displacement of the first branch 3 can be achieved by means of the first displacement means 5. The second displacement means 11 can be used to twist or rotate the second branch 6 towards or away from the first branch 3, wherein a displacement element 8 is arranged between the second branch 6 and the second displacement means 11.

If the first displacement means 5 is displaced to the outside of the component 2 or to the inside of the component 2, this movement is transmitted directly to the first branch 3, while the second branch 6 remains stationary in the axial direction. The branches 3, 6 move towards each other and a needle pinched between the branches 3, 6 can be rotated and optionally straightened.

Figure 2:
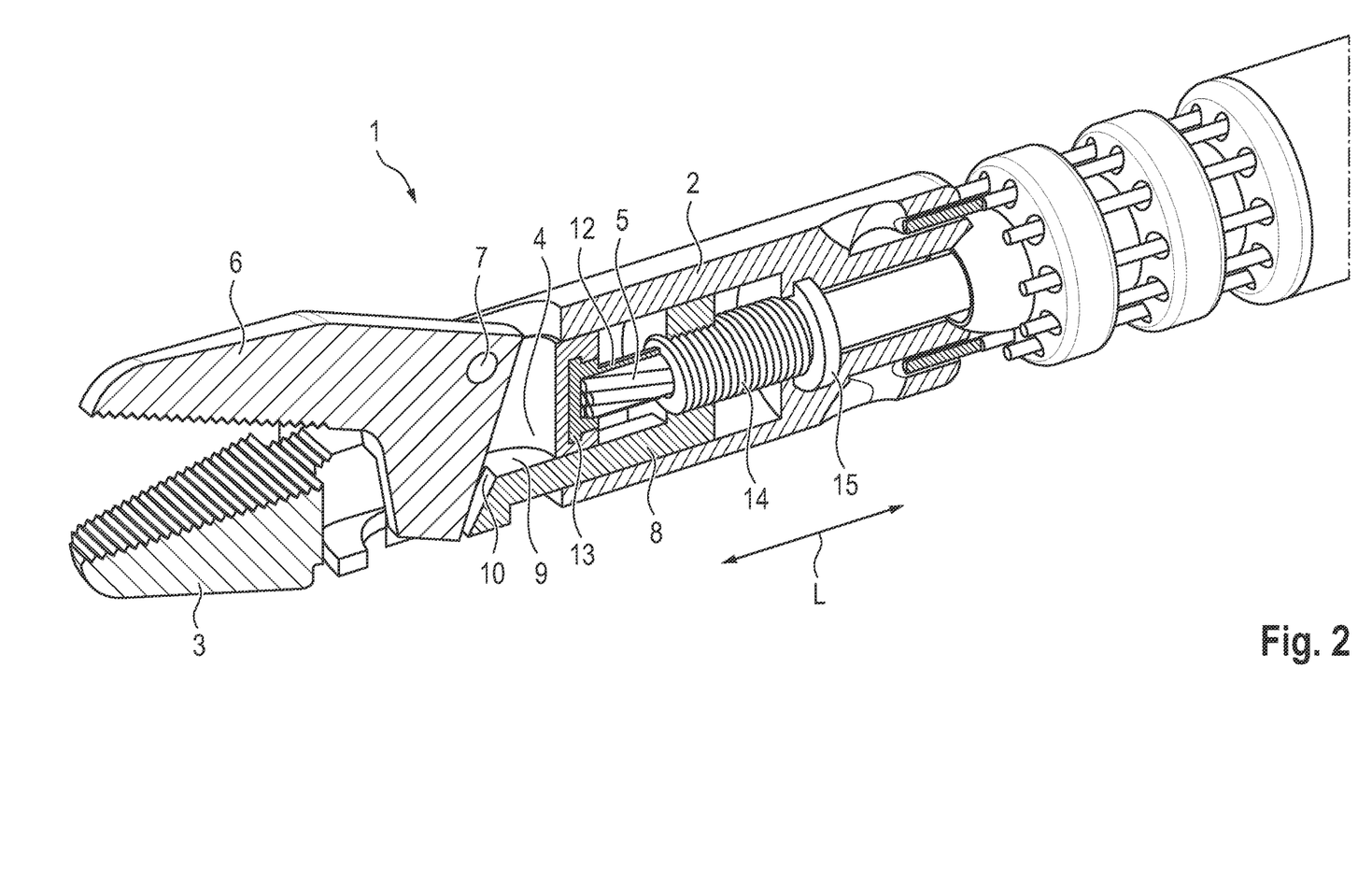
FIG. 2: a section through a second embodiment of an end effector.

The end effector 1 shown in FIG. 2 has a structure similar to the end effector according to FIG. 1. In contrast to FIG. 1, however, the end effector 1 according to FIG. 2 has only a first displacement means 5. The first displacement means 5 is rotatably connected to a first end of the first branch 3, wherein the displacement means 5 is arranged in a screw sleeve 14 in a rotationally fixed manner. The screw sleeve 14 is rotatably arranged in the displacement element 8, wherein the displacement element 8 has a counter-thread designed to complement the thread of the screw sleeve 14 in order to displace the displacement element 8. The first displacement means 5 is designed as a rope, in particular a wire rope.

The first displacement means 5 is arranged in a displacement means sleeve 12 having a collar 13. The displacement means 5 is connected to the displacement means sleeve 12 in a rotationally fixed manner. In other words, the displacement means sleeve 12 is arranged in the screw sleeve 14 in a rotationally fixed manner.

The screw sleeve 14 also has a collar 15. The screw sleeve 14 is arranged in the component 2 such that it can rotate. In other words, the screw sleeve 14 can be rotated, wherein the displacement element 8 is displaced along the direction of longitudinal extension L as a result of a rotation of the screw sleeve 14.

The end effector 1 is set up to displace the displacement element 8 in the direction of longitudinal extension L of the component 2 when the first displacement means 5 rotates about its longitudinal axis.

In addition to the known possibility of axial displacement of the first displacement means 5, the second embodiment of the end effector 1 uses its turning in order to control a second function. The first branch 3 is guided so that it can move axially within the component 2, so that a forward or backward movement of the first displacement means 5 displaces the first branch 3 in order to bring about the desired relative displacement between the two branches 3, 6. As mentioned above, as a result of a rotation of the first displacement means 5, the screw sleeve 14 is driven, which screws the displacement element 8 forwards or backwards, wherein the displacement element 8 enables the second branch 6 to be opened or closed.

The advantage of this embodiment is that the provision of the thread and the complementary counter-thread allows very high closing forces to be built up directly in the second branch 6. If the thread is self-locking, an object, such as a needle, can be gripped and properly clamp it.

Figure 3:
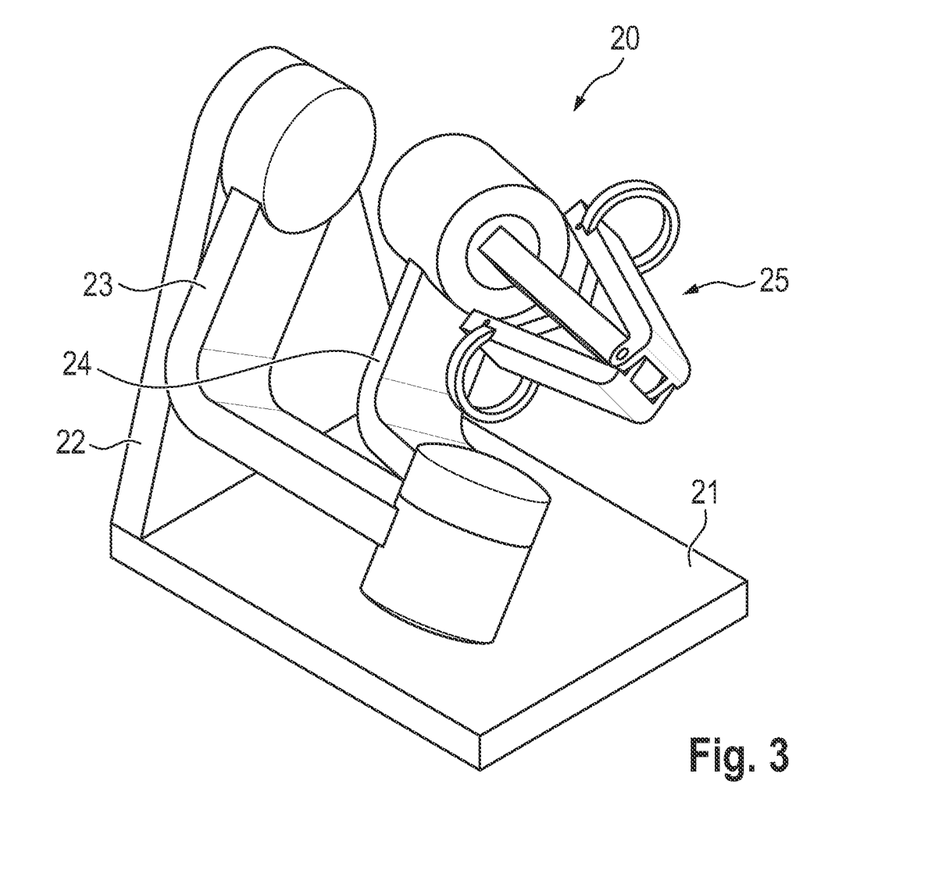
FIG. 3: a view of an embodiment of the device.
Figure 4:
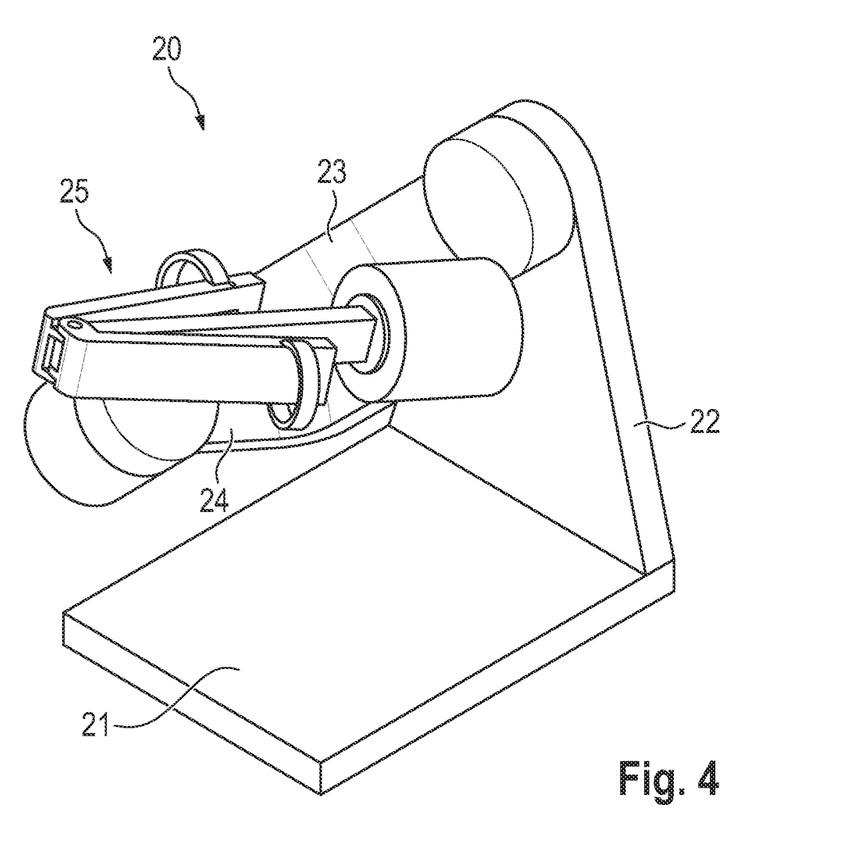
FIG. 4: a further view of the device from FIG. 3.
Figure 5:
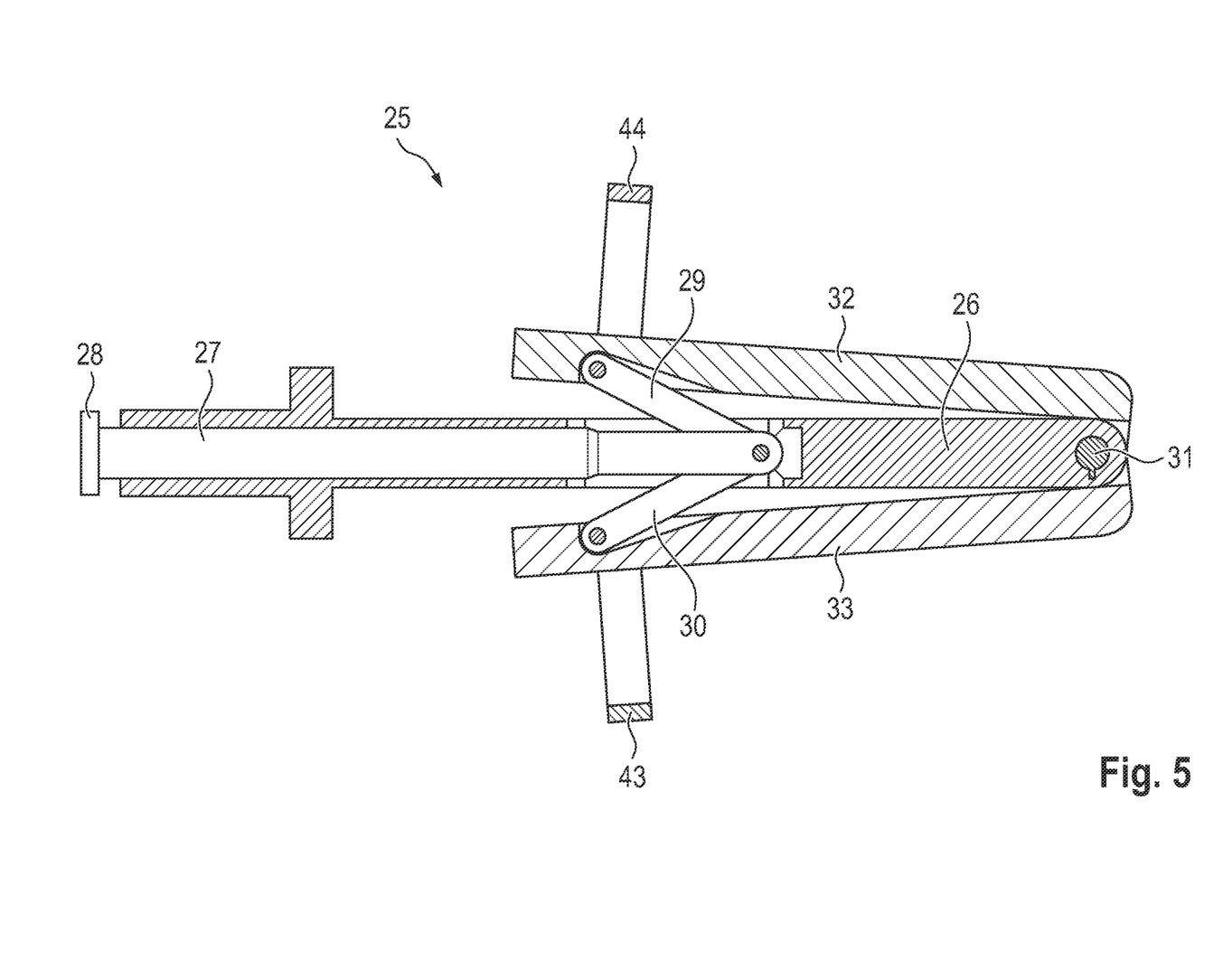
FIG. 5: a section through an operating element of the device from FIGS. 3 and 4.

A device 20 for controlling an end effector 1 is shown respectively in FIGS. 3 and 4. The device 20 comprises a foot 21, a first arm 22, a second arm 23, a third arm 24 and an operating element 25. The operating element 25 can also be understood as an input unit. The surgeon has the option of operating the respective device 20 with the thumb and another finger. The devices 20 are set up to detect the movements of the hands or fingers, wherein the positions of the hands or fingers and their orientation in space as well as the opening state of the operating elements 25 are transmitted to a controlling software and/or to a medical telemanipulation system (not shown). The device 20 particularly detects orientation changes in space, preferably roll, nod and yaw. The device 20 can advantageously be mounted as a whole in such a way that it can be moved laterally in all directions in order to ensure position detection in the overall system. The latter mounting of the device 20 is not shown in detail in FIGS. 3 and 4 for reasons of clarity. An operating element 25 is shown in FIG. 5. The operating element 25 comprises a housing 26 and two limbs 32, 33 arranged on the housing 26. The limbs 32, 33 are arranged on the housing 26 so as to be rotatable at a pivot point 31. A displaceably arranged component 27 is provided within the housing 26. A distal end 28 of the component 27 protrudes from the housing 26. Furthermore, the device 20 has two lugs 29, 30 connecting the limbs 32, 33 to the component 27 for actuating the component 27. As a result of the actuation of the component 27, the second branch 6 can be twisted or rotated in the direction towards the first branch 3 and/or in the direction away from the first branch 3.

For improved handling, the first limb 32 has a finger or thumb ring 43 and the second limb 33 has a finger or thumb ring 44.

Figure 6:
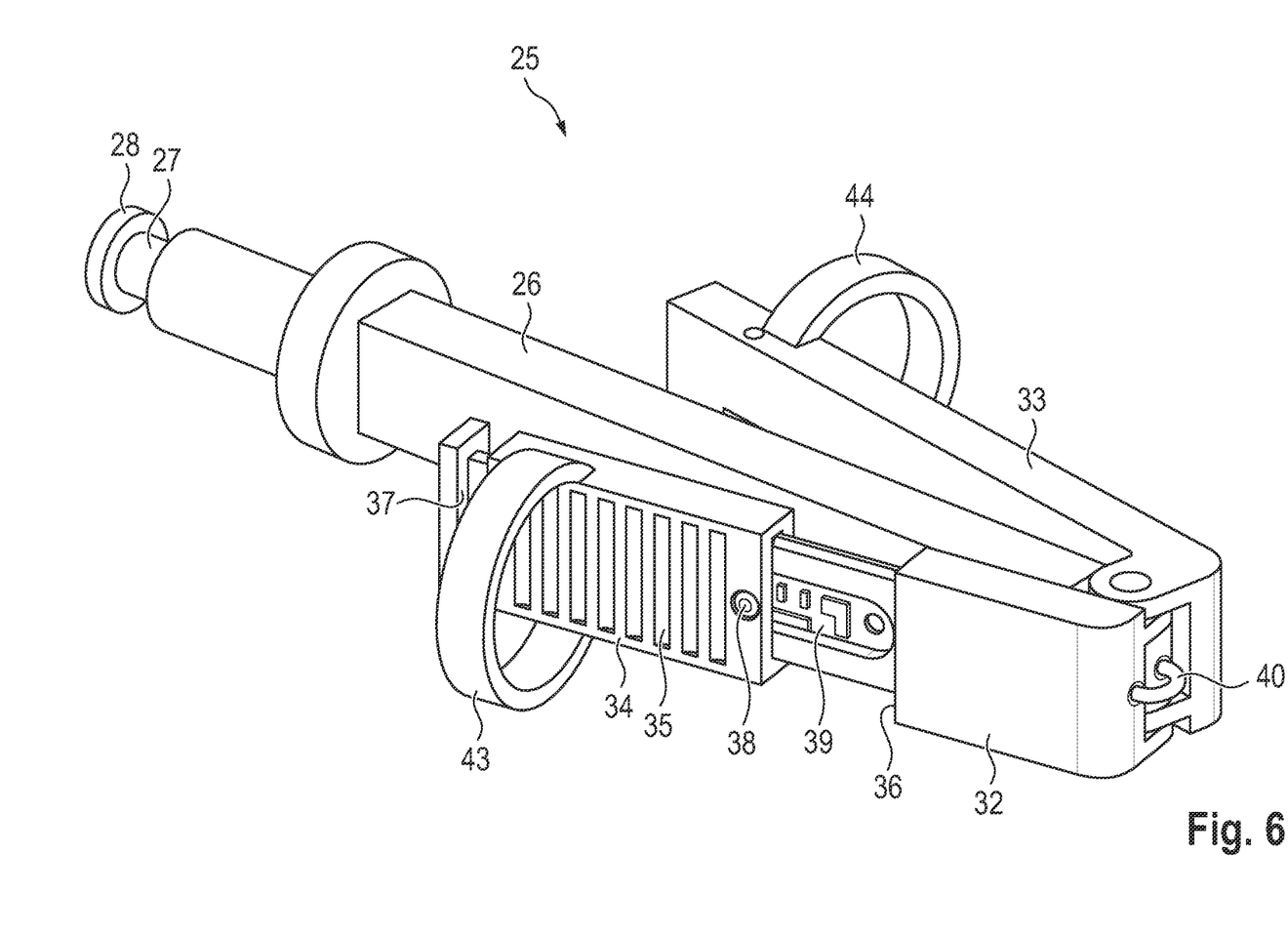
FIG. 6: a view of a first embodiment of an operating unit.

A first embodiment of the operating element 25 is shown in FIG. 6. In addition to the components shown in FIG. 5, at least one of the limbs 32, 33 has an actuating means 27. The actuating means 27 is set up to displace the first branch 3 relative to the second branch 6.

The actuating means 27 is designed as a slider 34. The slider 34 can be displaced along the longitudinal extension of the limb 32. In other words, the slider 34 is arranged to be displaceable along the limb 32.

The slider 34 has a corrugation 35. Furthermore, the slider 34 has two stops 36, 37 for limiting its displacement. In addition, a spring can be used to return the slider 34 to its initial position. Furthermore, a magnet 38 is integrated into the slider 34 and a displacement sensor 39 is integrated into the limb 32. A cable 40 is provided on the operating element 25 in order to transmit a displacement of the displacement sensor 39 to the first branch 3. In this way, the displacement or a displacement length of the slider 34 can be transmitted to the controlling software and/or to a medical telemanipulation system (not shown).

Figure 7:
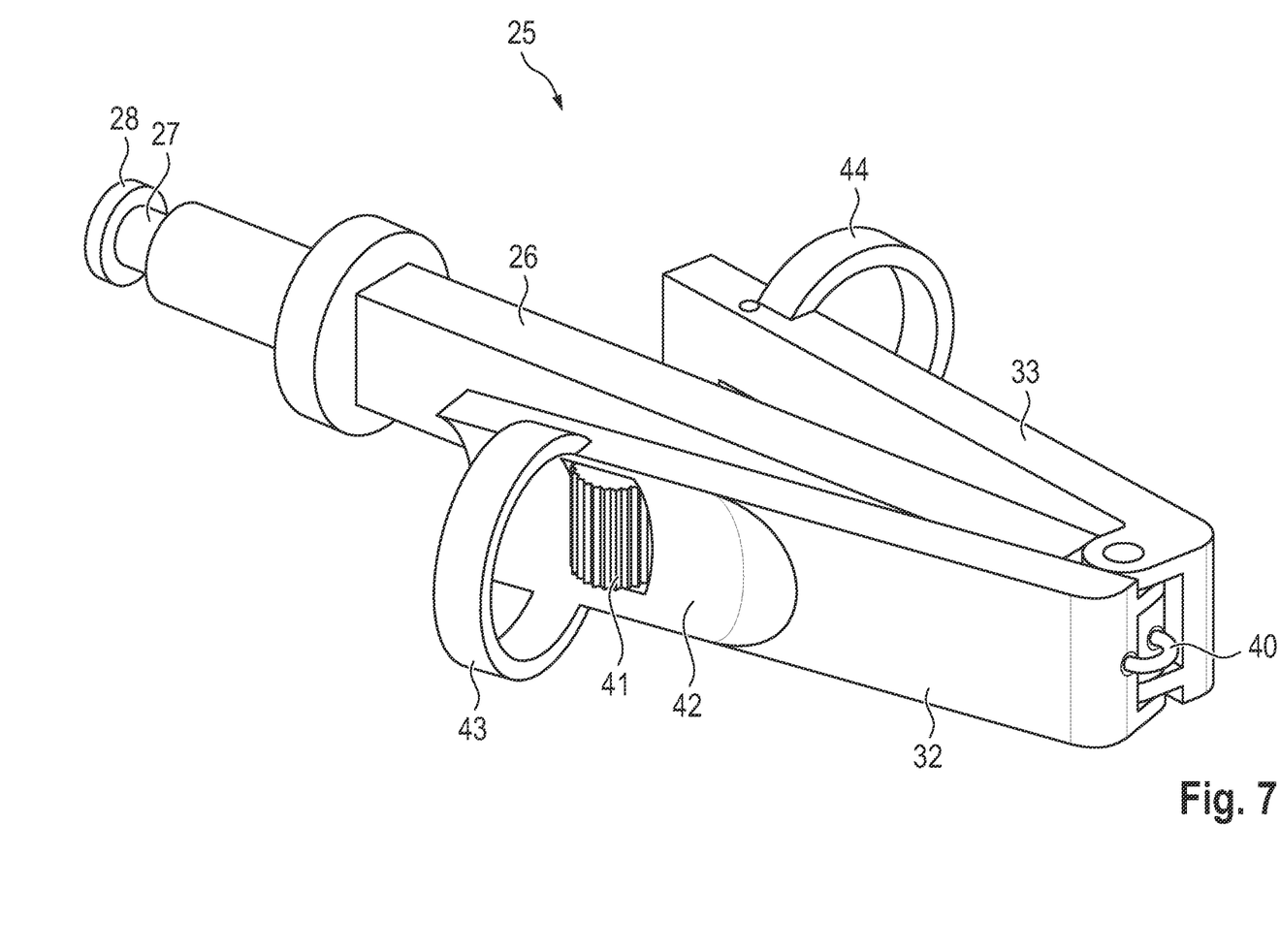
FIG. 7: a view of a second embodiment of the operating unit.

A second embodiment of the operating element 25 is shown in FIG. 7. In contrast to the first embodiment of the operating element 25 according to FIG. 6, a friction wheel 41 is used instead of the slider 34. The friction wheel 41 is integrated into the limb 32.

The friction wheel 41 is arranged in a recess 42 (trough) of the limb 32. Furthermore, the limb 32 or the friction wheel 41 has at least one stop (not shown for limiting a torsion or rotation of the friction wheel 41. Furthermore, a spring (not shown) can also be provided for returning the friction wheel 41 to its initial position. In addition, an angle sensor is integrated into the limb 32.

The angle sensor integrated into the limb 32 is set up to detect a rotation angle. The detected value can be transmitted with a cable 40 to control the displacement of the first branch 3. In this way, the angle of rotation or a torsion or rotation of the friction wheel 41 can be transmitted to the controlling software and/or to a medical telemanipulation system (not shown).

By means of the devices, it is possible to carry out a relative displacement of the first branch in relation to the second branch via a medical telemanipulation system. Furthermore, a torsion or rotation of the second branch relative to the first branch is possible. The branches can be moved relative to one another in order to rotate and, if necessary, erect an object that is clamped therein, such as a needle.

LIST OF REFERENCE NUMBERS

1 End effector
2 Component
3 Branch
4 Section
5 Displacement means
6 Branch
7 Pivot point, joint
8 Displacement element
9 Section
10 Stop
11 Displacement means
12 Displacement means sleeve
13 Collar
14 Screw sleeve
15 Collar
20 Device
21 Foot
22 Arm
23 Arm
24 Arm
25 Operating element
26 Housing
27 Actuating means
28 Distal end
29 Lug
30 Lug
31 Pivot point, joint
32 Limb
33 Limb
34 Slider
35 Corrugation
36 Stop
37 Stop
38 Magnet
39 Displacement sensor
40 Cable
41 Friction wheel
42 Recess
43 Finger or thumb ring
44 Finger or thumb ring

The invention claimed is:
1. An end effector, in particular a robot end effector comprising:
 a first branch,
 a second branch, and
 a component at least partially accommodating the two branches,
 wherein the first branch is displaceable relative to the second branch along a direction of longitudinal extension of the component, and the first branch is connected to a first rope configured for relative displacement, wherein a portion of the first rope is arranged in a rotationally fixed manner in a screw sleeve, and wherein the second branch is rotatably mounted on the component and configured to clamp an object between the two branches, and the second branch is rotatably connected to a displacement element to twist the second branch or the second branch bears rotatably on the displacement element.

2. The end effector according to claim 1, wherein, in order to displace the first branch relative to the second branch, the first branch has a section which is formed as a counterpart to a section of the displacement element.

3. The end effector according to claim 1, wherein the displacement element is connected to a second rope.

4. The end effector according to claim 1, wherein the end effector is configured to displace the displacement element in the direction of longitudinal extension of the component, when the second rope is displaced.

5. The end effector according to claim 1, wherein the first rope is rotatably connected to a first end of the first branch, wherein the screw sleeve is rotatably arranged in the displacement element and wherein for displacement of the displacement element the displacement element has a counter-thread designed to complement the thread of the screw sleeve.

6. The end effector according to claim 5, wherein the first rope is arranged in a rope sleeve having a collar and the first rope is rotationally fixed and connected to the rope sleeve.

7. The end effector according to claim 5, wherein the screw sleeve has a collar and the screw sleeve is arranged rotatably in the component.

8. The end effector according to claim 3, wherein the end effector is set up to displace the displacement element when the first rope rotates about a longitudinal axis of the first rope, in the direction of longitudinal extension of the component.

9. A device with an operating element configured to control an end effector according to claim 1.

10. The device according to claim 9, wherein the operating element has a housing and two limbs arranged at the housing and wherein at least one of the limbs has an actuator, wherein the actuator is configured to displace the first branch relative to the second branch.

11. The device according to claim 10, wherein the actuator is a slider, wherein the slider is displaceable along the longitudinal extension of the limb.

12. The device according to claim 11, wherein the limb comprises one or more of:
  a corrugation,
  at least one stop configured to limit a displacement of the slider,
  a spring configured to return the slider to an initial position, and
  a magnet is integrated into the slider and a displacement sensor is integrated into the limbs.

13. The device according to claim 10, wherein the actuator is a friction wheel, wherein the friction wheel is arranged in or at the limb.

14. The device according to claim 13, wherein one or more of:
  the friction wheel is arranged in a recess of the limb,
  the limb or the friction wheel comprises at least one stop configured to limit a rotation of the friction wheel,
  a spring is configured to return the friction wheel to an initial position, and
  an angle sensor is integrated into the limbs.

15. A robot with at least one end effector according to claim 1.

16. A medical telemanipulation system comprising at least one device according to claim 9.

17. A robot with at least one device according to claim 9.

18. A medical telemanipulation system comprising a robot according to claim 15.

19. The device according to claim 1, wherein the end effector is a robot end effector.

* * * * *